United States Patent [19]

Fest et al.

[11] Patent Number: 4,911,752
[45] Date of Patent: Mar. 27, 1990

[54] HALOGENOALKOXY-PHENYLSUL-PHONYLISOTHIOUREIDOAZINE HERBICIDAL AGENTS

[75] Inventors: Christa Fest, Wuppertal; Klaus-Helmut Müller, Duesseldorf; Theodor Pfister, Monheim; Hans-Jochem Riebel, Wuppertal; Hans-Joachim Santel, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 170,613

[22] Filed: Mar. 15, 1988

Related U.S. Application Data

[63] Continuation of Ser. No. 2,073, Jan. 12, 1987, abandoned.

[30] Foreign Application Priority Data

Jan. 22, 1986 [DE] Fed. Rep. of Germany ....... 3601801

[51] Int. Cl.$^4$ ............................................. A01N 43/66
[52] U.S. Cl. ............................................ 71/93; 71/92; 71/94
[58] Field of Search ............................................ 71/93

[56] References Cited

U.S. PATENT DOCUMENTS

| | | | |
|---|---|---|---|
| 4,452,628 | 6/1984 | Adams ................................ | 71/93 |
| 4,479,821 | 10/1984 | Meyers et al. ..................... | 71/93 |
| 4,492,598 | 1/1985 | Willms et al. ..................... | 71/93 |

FOREIGN PATENT DOCUMENTS 0005986 12/1979 European Pat. Off. ............ 71/92

*Primary Examiner*—Catherine L. Mills
*Attorney, Agent, or Firm*—Sprung Horn Kramer & Woods

[57] ABSTRACT

A method of combating unwanted vegetation which comprises applying to such vegetation or to a locus from which it is desired to exclude such vegetation a herbicidally effective amount of a halogenoalkoxy-phenylsulphonylisothioureidoazine of the formula

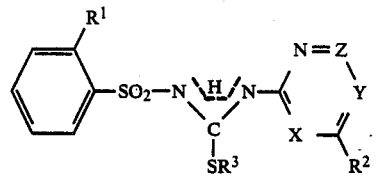

in which $R^1$ represents halogeno-$C_1$-$C_4$-alkoxy, $R^2$ represents hydrogen, halogen, hydroxyl, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, $C_1$-$C_4$-halogenoalkylthio, amino, $C_1$-$C_4$-alkyl-amino or di-($C_1$-$C_4$-alkyl)-amino, X represents nitrogen or a —CH— grouping, Y represents nitrogen or a —$CR^4$— grouping, wherein $R^4$ represents hydrogen, halogen, cyano, $C_1$-$C_4$-alkyl, formyl, $C_1$-$C_4$-alkyl-carbonyl or $C_1$-$C_4$-alkoxy-carbonyl, and Z represents nitrogen or a —$CR^5$— grouping, wherein $R^5$ represents hydrogen, halogen, hydroxyl, $C_1$-$C_4$-alkyl, $C_1$-$C_4$-alkoxy, $C_1$-$C_4$-alkylthio, $C_1$-$C_4$-alkylamino or di-($C_1$-$C_4$-alkyl)-amino, and $R^3$ represents $C_1$-$C_{10}$-alkyl (which is optionally substituted by fluorine, chlorine, bromine, cyano, $C_1$-$C_4$-alkoxy, carboxyl, $C_1$-$C_4$-alkoxycarbonyl, aminocarbonyl, $C_1$-$C_4$-alkylaminocarbonyl or di-($C_1$-$C_4$-alkyl)-amino-carbonyl), or represents $C_2$-$C_6$-alkenyl (which is optionally substituted by fluorine, chlorine and/or bromine) or $C_2$-$C_6$-alkinyl, or represents phenyl-$C_1$-$C_2$-alkyl (which is optionally substituted in the phenyl part by fluorine, chlorine, bromine, nitro, cyano, $C_1$-$C_4$-alkyl, $C_1$-$C_4$-alkoxy or $C_1$-$C_4$-alkoxycarbonyl).

6 Claims, No Drawings

HALOGENOALKOXY-PHENYLSULPHONYLISO-THIOUREIDOAZINE HERBICIDAL AGENTS

This application is a continuation of application Ser. No. 002,073, filed Jan. 12, 1987, abandoned.

The present invention relates to the use of halogenoalkoxyphenylsulphonylisothioureidoazines as herbicides.

Various isothioureas, such as, for example, N'-(4,6-dimethoxypyrimidin-2-yl)-N''-(2-chloro-benzenesulphonyl)-S-methyl-isothiourea, have been disclosed as potential herbicides, but have hitherto achieved no relatively great importance as agents for combating weeds and/or regulating plant growth (compare European Patent A 5,986).

It has now been found that the halogenoalkoxyphenylsulphonylisothioureidoazines of the general formula (I)

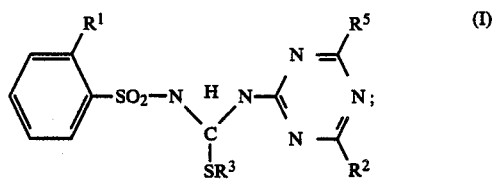

in which
R$^1$ represents halogeno-C$_1$-C$_4$-alkoxy,
R$^2$ represents hydrogen, halogen, hydroxyl, C$_1$-C$_4$-alkyl, C$_1$-C$_4$-halogenoalkyl, C$_1$-C$_4$-alkoxy, C$_1$-C$_4$-halogenoalkoxy, C$_1$-C$_4$-alkylthio, C$_1$-C$_4$-halogenoalkylthio, amino, C$_1$-C$_4$-alkylamino or di-(C$_1$-C$_4$-alkyl)-amino,
R$^5$ represents hydrogen, halogen, hydroxyl, C$_1$-C$_4$-alkyl, C$_1$-C$_4$-alkoxy, C$_1$-C$_4$-alkylthio, C$_1$-C$_4$-alkylamino or di-(C$_1$-C$_4$-alkyl)-amino,
and in which, furthermore,
R$^3$ represents C$_1$-C$_{10}$-alkyl (which is optionally substituted by fluorine, chlorine, bromine, cyano, C$_1$-C$_4$-alkoxy, carboxyl, C$_1$-C$_4$-alkoxycarbonyl, aminocarbonyl, C$_1$-C$_4$-alkylaminocarbonyl or di-(C$_1$-C$_4$-alkyl)-amino-carbonyl), or represents C$_2$-C$_6$-alkenyl (which is optionally substituted by fluorine, chlorine and/or bromine) or C$_2$-C$_6$-alkinyl, or represents phenyl-C$_1$-C$_2$-alkyl (which is optionally substituted in the phenyl part by fluorine, chlorine, bromine, nitro, cyano, C$_1$-C$_4$-alkyl, C$_1$-C$_4$-alkoxy or C$_1$-C$_4$-alkoxycarbonyl),
are particularly suitable for combating weeds, in particular (weeds) in monocotyledon crops.

Surprisingly, the halogenoalkoxyphenylsulphonylisothioureidoazines to be used according to the invention exhibit, for example when used in important crop plants, a substantially better action against weeds than the isothioureas known from the prior art, such as, for example, N'-(4,6-dimethoxy-pyrimidin-2-yl)-N''-(2-chloro-benzenesulphonyl)-S-methyl-isothiourea (compare European Patent A 5,986).

Formula (I) provides a general definition of the halogenoalkoxyphenylsulphonylisothioureidoazines to be used according to the invention. In this formula, preferably,
R$^1$ represents halogeno-C$_1$-C$_2$-alkoxy with up to 5 halogen atoms, such as fluorine and/or chlorine, in the alkyl part,
R$^2$ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino,
X represents nitrogen or a —CH— grouping,
Y represents nitrogen or a —CR$^4$— grouping, wherein
R$^4$ represents hydrogen, fluorine, chlorine, bromine, cyano, methyl, formyl, acetyl, methoxycarbonyl or ethoxycarbonyl, and
Z represents nitrogen or a —CR$^5$— grouping, wherein
R$^5$ represents hydrogen, fluorine, chlorine, bromine, methyl, ethyl, methoxy, ethoxy, propoxy, isopropoxy, methylthio, ethylthio, methylamino, ethylamino, dimethylamino or diethylamino, and
R$^3$ represents C$_1$-C$_6$-alkyl (which is optionally substituted by fluorine, chlorine, bromine, cyano, C$_1$-C$_2$-alkoxy, carboxyl, C$_1$-C$_2$-alkoxycarbonyl, aminocarbonyl, C$_1$-C$_2$-alkylamino-carbonyl or di-(C$_1$-C$_2$-alkyl)-amino-carbonyl) or represents C$_3$-C$_4$-alkenyl (which is optionally substituted by fluorine, chlorine and/or bromine) or C$_3$-C$_4$-alkinyl, or represents benzyl or phenethyl (which are optionally substituted in the phenyl part by fluorine, chlorine, bromine, nitro, C$_1$-C$_2$-alkyl, C$_1$-C$_2$-alkoxy or C$_1$-C$_2$-alkoxycarbonyl).

Particularly preferred compounds of the formula (I) which are used are those in which
R$^1$ represents difluoromethoxy, trifluoromethoxy, 2-fluoro-1-ethoxy or 2-chloro-1-ethoxy,
R$^2$ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino,
X represents nitrogen or a —CH— grouping,
Y represents nitrogen or a —CR$^4$— grouping,
R$^4$ represents hydrogen, fluorine, chlorine, bromine, cyano, methyl, formyl, acetyl, methoxycarbonyl or ethoxycarbonyl, and
Z represents nitrogen or a —CR$^5$— grouping, wherein
R$^5$ represents hydrogen, fluorine, chlorine, bromine, methyl, ethyl, methoxy, ethoxy, propoxy, isopropoxy, methylthio, ethylthio, methylamino, ethylamino, dimethylamino or diethylamino, and
R$^3$ represents C$_1$-C$_3$-alkyl, C$_1$-C$_2$-alkoxycarbonylmethyl or benzyl.

Compounds of the formula (I) which are especially preferably used are those in which
R$^1$ represents trifluoromethoxy and
R$^2$, X, Y, Z and R$^3$ have the abovementioned particularly preferred meanings.

The halogenoalkoxyphenylsulphonylisothioureidoazines of the formula (I) to be used according to the invention are the subject of application Ser. No. 769,272, filed August 23, 1985, now pending, application Ser. No. 769,271 filed August 23, 1985, now pending, and application Ser. No. 769,222, filed August 23, 1985, now pending, corresponding respectively to German Patent Application P 3,517,844, P 3,517,842 and P 3,517,821.

The compounds of the formula (I) are obtained by a process in which
(a) N-sulphonyl-imino-dithiocarbonic acid esters of the formula (II)

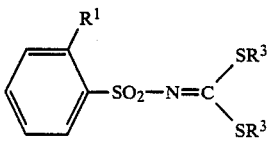

in which

R¹ and R³ have the abovementioned meanings, are reacted with amines of the formula (III)

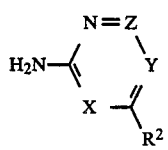

in which

R², X, Y and Z have the abovementioned meanings, if appropriate in the presence of bases, such as, for example, sodium hydride or potassium tert.-butylate, and if appropriate in the presence of diluents, such as, for example, tetrahydrofuran, dioxane or dimethylformamide, at temperatures between 0° C. and 100° C., and when the reaction has ended the mixture is diluted with water and acidified with a strong acid, such as, for example, hydrochloric acid, and the products of the formula (I) obtained as crystals are isolated by filtration with suction; or (b) sulphonylguanidines of the formula (IV)

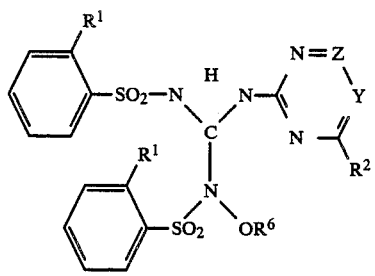

in which

R¹, R², X, Y and Z have the abovementioned meanings and

R⁶ represents $C_1$-$C_4$-alkyl or benzyl, are reacted with mercaptans of the formula (V)

$$R^3SH \qquad (V)$$

in which

R³ has the abovementioned meaning, if appropriate in the presence of acid acceptors, such as, for example, triethylamine, sodium methylate or pyrazole, and if appropriate in the presence of diluents, such as methanol, ethanol or i-propanol, at temperatures between 0° C. and 150° C., and , when the reaction has ended, if appropriate, the mixture is acidified with an acid, such as, for example, glacial acetic acid and the reaction product is worked up by customary methods.

Formula (II) provides a general definition of the N-sulphonyl-imino-dithiocarbonic acid esters required as starting substances in process variant (a). In formula (II), R¹ and R³ preferably or particularly have the same meanings as have been given as preferred or as particularly preferred above in the context of the definition of substituents for formula (I).

The N-sulphonyl-imino-dithiocarbonic acid esters of the formula (II) can be prepared by processes which are known per se (compare Chem. Ber. 99 (1966), 2855 and EP-OS (European Published Specification) 5,986).

Formula (III) provides a general definition of the amines furthermore to be employed as starting substances for process variant (a). In formula (III), X, Y, Z and R² preferably or particularly have the same meanings as have been given as preferred or as particularly preferred above in the context of the substituent definition for formula (I).

The amines of the formula (III) are known and/or can be prepared by processes which are known per se.

Formula (IV) provides a general definition of the sulphonylguanidines required as starting substances for process (b). In formula (IV), R¹, R², X, Y and Z preferably or particularly have the same meanings as are given as preferred or as particularly preferred above in the context of the definition of substituents for formula (I). R⁶ in this formula represents $C_1$-$C_4$-alkyl or benzyl, preferably methyl or benzyl.

The compounds of the formula (IV) are known and/or can be prepared by known processes. (See U.S. Pat. No. 4,602,938).

Formula (V) provides a general definition of the mercaptans furthermore required as starting substances for process (b). In formula (V), R³ preferably or particularly has the same meanings as are given as preferred or as particularly preferred above in the context of the definition of substituents for formula (I).

The mercaptans of the formula (V) are generally known compounds of organic chemistry.

The compounds of the formula (I) to be used according to the invention are particularly suitable for selectively combating monocotyledon and dicotyledon weeds, in particular in monocotyledon crops, such as, for example, wheat and corn.

The active compounds to be used according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds to be used according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example Ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds, as such or in the form of their formulations, can also be used, for combating weeds, as mixtures with known herbicides, finished formulations or tank mixes being possible.

Possible components for the mixtures are known herbicides, such as, for example, N-(2-benzothiazolyl)-N,N'-dimethylurea, 3-(3-chloro-4-methylphenyl)-1,1-dimethylurea, 3-(4-isopropylphenyl)-1,1-dimethylurea, 2-chloro-N-{[4-methoxy-6-methyl-1,3,5-triazin-2-yl)-amino]carbonyl}-benzenesulphonamide, ethyl 2-{[(4-chloro-6-methoxy-2-pyrimidyl)-aminocarbonyl]aminosulphonyl}benzoate, 2-ethylamino-6-(1,1-dimethylethyl-amino)-4-methylthio-1,3,5-triazine, 4-amino-6-(1,1-dimethylethyl)-3-methylthio-1,2,4-triazin-5(4H)-one, 4-amino-6-(1,1-dimethylethyl)-3-ethylthio-1,2,4-triazin-5(4H)-one, 1-amino-6-ethylthio-3-(2,2-dimethylpropyl)-1,3,5-triazine-2,4-(1H,3H)-dione, 5-(2-chloro-4-trifluoromethyl-phenoxy)-N-methylsulphonyl-2-nitrobenzamide, 2-ethoxy-1-methyl-2-oxo-ethyl 5-(2-chloro-4-trifluoromethyl-phenoxy)-2-nitrobenzoate, methyl 2-[4-(2,4-dichlorophenoxy)-phenoxy]propionate, 2-{4-[(3-chloro-5-trifluoromethyl-2-pyridinyl)oxy]-phenoxy}-propionic acid, the R enantiomer of (trimethylsilyl)-methyl 2-{4-[(3,5-dichloropyridin-2-yl)oxy]phenoxy}-propionate, 2,4-dichlorophenoxyacetic acid, 2-(2,4-dichlorophenoxy)-propionic acid, 4-chloro-2-methyl-phenoxy-acetic acid, 2-(4-chloro-2-methyl-phenoxy)-propionic acid, 3,5-diiodo-4-hydroxy-benzonitrile, 3,5-dibromo-4-hydroxy-benzonitrile, 2-[5-methyl-5-(1-methylethyl)-4-oxo-2-imidazolin-2-yl]-3-pyridinecarboxylic acid, 2-(1-ethoxyamino-butylidene)-5-(2-ethylthiopropyl)-1,3-cyclohexanedione, [(4-amino-3,5-dichloro-6-fluoro-2-pyridinyl)oxy]-acetic acid and 3-isopropyl-2,1,3-benzothiadiazin-4-one 2,2-dioxide. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds can be seen from the following examples.

EXAMPLE A

Pre-emergence test/greenhouse
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the compounds of preparation Examples (7) and (9) show a better herbicidal activity than comparison compound (A).

EXAMPLE B

Post-emergence test/greenhouse
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 L of water/ha. After three weeks, the degree of damage to the plants is rated in % damage in comparison to the development of the untreated control. The figures denote:

0% = no action (like untreated control)
100% = total destruction

In this test, for example, the compounds of preparation Examples (7) and (9) show a very good tolerance in crop plants, such as, for example, corn and wheat and at the same time a greater activity against weeds, such as, for example, Matricaria, Chenopodium and Polygonum, than comparison compound (A).

TABLE A

| Active compound | Amount of active compound applied kg/ha | Wheat | Datura | Stellaria | Matricaria | Alopecurus | Lolium |
|---|---|---|---|---|---|---|---|
| (A) (known) | 0.5 | 0 | 0 | 0 | 30 | 20 | 0 |
| (7) | 0.5 | 0 | 80 | 90 | 90 | 90 | 90 |
| (9) | 0.5 | 0 | 80 | 90 | 90 | 80 | 80 |

(A) 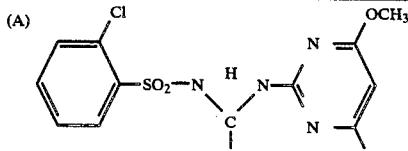

(7) 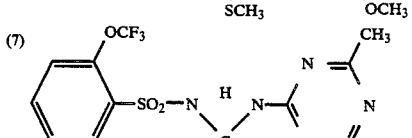

(9) 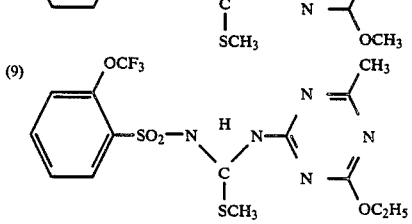

TABLE B

| Active compound | Amount of active compound applied kg/ha | Corn | Wheat | Chenopodium | Matricaria | Polygonum | Sinapis |
|---|---|---|---|---|---|---|---|
| (A) (known) | 0.5 | 0 | 0 | 40 | 0 | 10 | 80 |
| (7) | 0.25 | 0 | 0 | 100 | 100 | 100 | 100 |

TABLE B-continued

| | | Post-emergence test/greenhouse | | | | | |
|---|---|---|---|---|---|---|---|
| Active compound | Amount of active compound applied kg/ha | Corn | Wheat | Chenopodium | Matricaria | Polygonum | Sinapis |
| (9) | 0.5 | 0 | 0 | 100 | 100 | 70 | 100 |

(A), (7), (9) [chemical structures]

PREPARATION EXAMPLES

Example 1

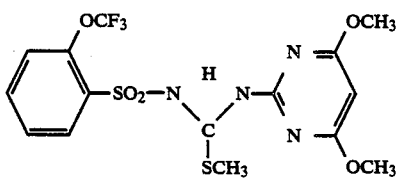

(Process (a))

A suspension of 3.0 g (0.1 mol) of sodium hydride (in oil) is added to a mixture of 7.8 g (0.05 mol) of 2-amino-4,6-dimethoxy-pyrimidine, while stirring, and the mixture is stirred at 20° C. for 12 hours. 17.3 g (0.05 mol) of N-(2-trifluoromethoxy-benzenesulphonyl)-S', S''-dimethyl-iminodithiocarbonic acid ester are then added in portions to the reaction mixture so that the reaction temperature does not rise above 40° C. After the mixture has been stirred at 20° C. for five hours, 1 l of ice-water is added and the mixture is filtered. The filtrate is acidified with concentrated hydrochloric acid, the product which is thereby obtained as crystals is isolated by filtration with suction and taken up in methylene chloride and the methylene chloride mixture is washed with water, dried and concentrated.

Recrystallization from ethanol gives 8.8 g (38.9% of theory) of N'-(4,6-dimethoxy-pyrimidin-2-yl)-N'''-(2-trifluoromethoxy-benzenesulphonyl)-S-methyl-isothiourea as white crystals of melting point 137° C.

Example 2

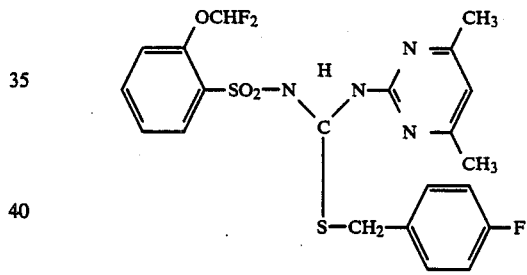

(Process (b))

A mixture of 6.1 g (0.01 mol) of N'-(4,6-dimethyl-pyrimidin-2-yl)-N'''-methoxy-N''', N''''-bis-(2-difluoromethoxybenzenesulphonyl)-guanidine, 1.1 g (0.02 mol) of sodium methylate, 2.8 g (0.02 mol) of 4-fluorobenzylmercaptan and 20 ml of ethanol is stirred at 60° C. for 15 hours. It is then acidified with glacial acetic acid and taken up in methylene chloride and the resulting mixture is washed twice with water, dried and concentrated.

Recrystallization from ethanol gives 1.3 g (27% of theory) of N'-(4,6-dimethyl-pyrimidin-2-yl)-N''-(2-difluoromethoxy-benzenesulphonyl)-S-(4-fluoro-benzyl)-isothiourea of melting point 156° C.

The following compounds of the formula (I)

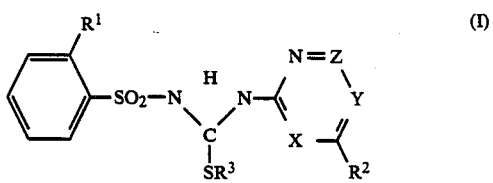

(I)

can be obtained analogously to Example 1 and 2:

TABLE 1

| Example No. | R¹ | R³ | (heterocycle with R²) | Melting point [°C.] |
|---|---|---|---|---|
| 3 | —OCF₃ | CH₃ | pyrimidine with OC₂H₅ (top) and OC₂H₅ (bottom) | 190 |
| 4 | —OCF₃ | CH₃ | pyrimidine with CH₃ (top) and CH₃ (bottom) | 122 |
| 5 | —OCF₃ | CH₃ | pyrimidine with OCHF₂ (top) and CH₃ (bottom) | 91 |
| 6 | —OCF₃ | CH₃ | pyrimidine with SCH₃ (top) and CH₃ (bottom) | 139 |
| 7 | —OCF₃ | CH₃ | triazine with OCH₃ and CH₃ | 120 |
| 8 | —OCF₃ | CH₃ | triazine with SCH₃ and CH₃ | 142 |
| 9 | —OCF₃ | CH₃ | triazine with OC₂H₅ and CH₃ | 103 |
| 10 | —OCF₃ | CH₃ | pyrimidine with CH₃ (top) and OCH₃ (bottom) | 138 |

TABLE 1-continued
| Example No. | $R^1$ | $R^3$ | ![structure](N=Z, Y, X, R²) | Melting point [°C.] |
|---|---|---|---|---|
| 11 | —OCF₃ | CH₃ | 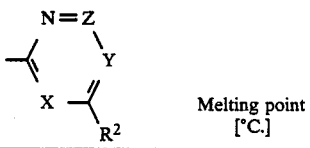 | 117 |
| 12 | —OCHF₂ | 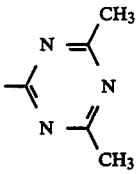 | 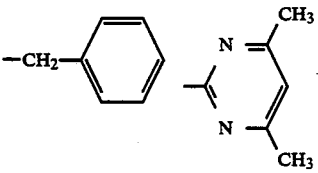 | 167 |
| 13 | —OCF₃ | CH₃ | 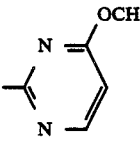 | 105 |
| 14 | —OCH₂CH₂Cl | CH₃ | 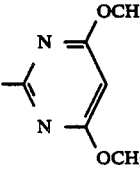 | |
| 15 | —OCH₂CH₂Cl | CH₃ | 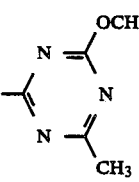 | |
| 16 | —OCH₂CH₂Cl | CH₃ | 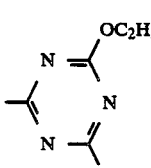 | |
| 17 | —OCF₃ | —CH₂COOCH₃ | 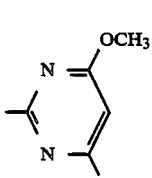 | |
| 18 | —OCF₃ | —CH₂COOCH₃ | 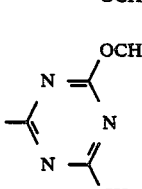 | |

TABLE 1-continued
| Example No. | R¹ | R³ | ![structure](N=Z, Y, X, R²) | Melting point [°C.] |
|---|---|---|---|---|
| 19 | —OCF₃ | —CH₂COOCH₃ | 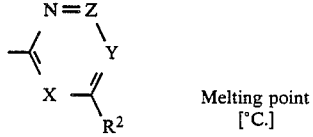 | |
| 20 | —OCHF₂ | CH₃ | 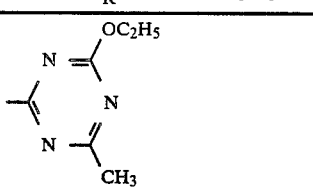 | |
| 21 | —OCHF₂ | CH₃ | 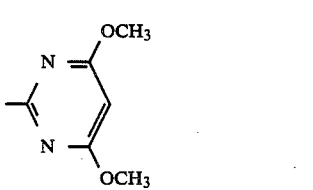 | |
| 22 | —OCHF₂ | CH₃ | 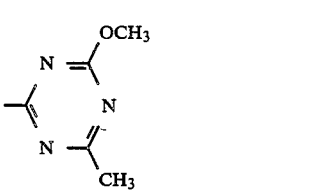 | |
| 23 | —OCF₃ | 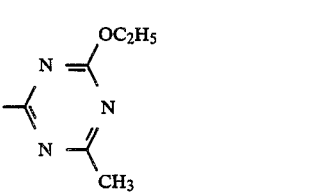 | 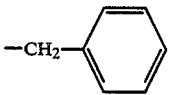 | |
| 24 | —OCF₃ | 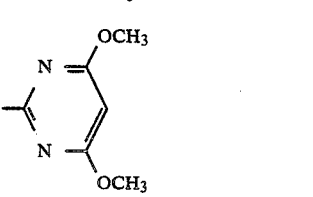 | 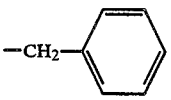 | |
| 25 | —OCF₃ | 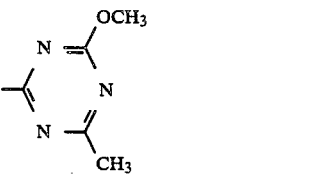 | 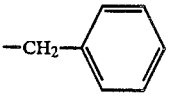 | |
| 26 | —OCF₃ | —C₂H₅ | 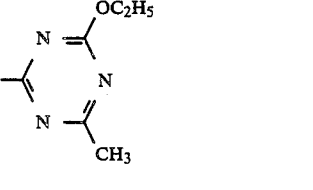 | 108 |
It is understood that the specification and examples are illustrative but not limitative of the present inven-

We claim:
1. A method of combating unwanted vegetation which comprises applying to such vegetation or to a locus from which it is desired to exclude such vegetation a herbicidally effective amount of a halogenoalkoxyphenylsulphonylisothioureidoazine of the formula

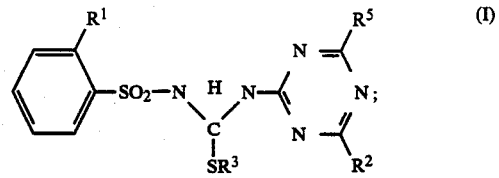

in which
R$^1$ represents difluoromethoxy or trifluoromethoxy,
R$^2$ represents hydrogen, halogen, hydroxyl, C$_1$-C$_4$-alkyl, C$_1$-C$_4$-halogenoalkyl, C$_1$-C$_4$-alkoxy, C$_1$-C$_4$-halogenoalkoxy, C$_1$-C$_4$-alkylthio, C$_1$-C$_4$-halogenoalkylthio, amino, C$_1$-C$_4$-alkylamino or di-(C$_1$-C$_4$-alkyl)-amino,
wherein
R$^5$ represents hydrogen, halogen, hydroxyl, C$_1$-C$_4$-alkyl, C$_1$-C$_4$-alkoxy, C$_1$-C$_4$-alkylthio, C$_1$-C$_4$-alkylamino or di-(C$_1$-C$_4$-alkyl)-amino, and
R$^3$ represents C$_1$-C$_{10}$-alkyl (which is optionally substituted by fluorine, chlorine, bromine, cyano, C$_1$-C$_4$-alkoxy, carboxyl, C$_1$-C$_4$-alkoxycarbonyl, aminocarbonyl, C$_1$-C$_4$-alkylaminocarbonyl or di-(C$_1$-C$_4$-alkyl)-amino-carbonyl), or represents C$_2$-C$_6$-alkenyl (which is optionally substituted by fluorine, chlorine and/or bromine) or C$_2$-C$_6$-alkinyl, or represents phenyl-C$_1$-C$_2$-alkyl (which is optionally substituted in the phenyl part by fluorine, chlorine, bromine, nitro, cyano, C$_1$-C$_4$-alkyl, C$_1$-C$_4$-alkoxy or C$_1$-C$_4$-alkoxycarbonyl).

2. The method according to claim 1, in which
R$^2$ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino,, and
R$^5$ represents hydrogen, fluorine, chlorine, bromine, methyl, ethyl, methoxy, ethoxy, propoxy, isopropoxy, methylthio, ethylthio, methylamino, ethylamino, dimethylamino or diethylamino, and
R$^3$ represents C$_1$-C$_6$-alkyl (which is optionally substituted by fluorine, chlorine, bromine, cyano, C$_1$-C$_2$-alkoxy, carboxyl, C$_1$-C$_2$-alkoxycarbonyl, aminocarbonyl, C$_1$-C$_2$-alkylamino-carbonyl or di-(C$_1$-C$_2$-alkyl)-amino-carbonyl) or represents C$_3$-C$_4$-alkenyl (which is optionally substituted by fluorine, chlorine and/or bromine) or C$_3$-C$_4$-alkinyl, or represents benzyl or phenethyl (which are optionally substituted in the phenyl part by fluorine, chlorine, bromine, nitro, C$_1$-C$_2$-alkyl, C$_1$-C$_2$-alkoxy or C$_1$-C$_2$-alkoxycarbonyl).

3. The method according to claim 1, in which
R$^2$ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino, and
R$^5$ represents hydrogen, fluorine, chlorine, bromine, methyl, ethyl, methoxy, ethoxy, propoxy, isopropoxy, methylthio, ethylthio, methylamino, ethylamino, dimethylamino or diethylamino, and
R$^3$ represents C$_1$-C$_3$-alkyl, C$_1$-C$_2$-alkoxycarbonyl-methyl or benzyl.

4. The method according to claim 3, in which R$^1$ represents trifluoromethoxy.

5. The method according to claim 1, wherein such compound is N'-(4-methoxy-6-methyl-triazin-2-yl)-N''-(2-trifluoromethoxy-benzenesulphonyl)-S-methyl-isothiourea of the formula

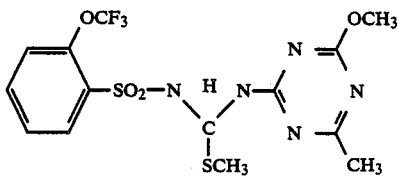

6. The method according to claim 1, wherein such compound is N'-(4-ethoxy-6-methyl-triazin-2-yl)-N''-(2-trifluoromethoxy-benzenesulphonyl)-S-methyl-isothiourea of the formula

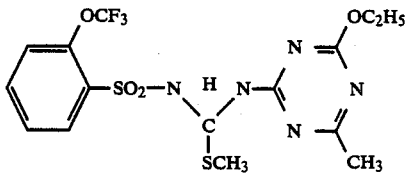

* * * * *

UNITED STATES PATENT AND TRADEMARK OFFICE
CERTIFICATE OF CORRECTION

PATENT NO. : 4,911,752

DATED : March 27, 1990

INVENTOR(S) : Fest et al.

It is certified that error appears in the above-identified patent and that said Letters Patent is hereby corrected as shown below:

Col. 18, line 32, claim 5 Delete middle of formula
$$\text{"N}\underset{\underset{SR^3}{|}}{\underset{C}{\diagdown\diagup}}\text{N"}$$
and substitute
$$-- \text{N}\underset{\underset{SR^3}{|}}{\underset{C}{\diagdown\diagup}}^{H}\text{N} --$$

Col. 18, line 45, claim 6 Delete middle of formula
$$\text{"N}\underset{\underset{SCH_3}{|}}{\underset{C}{\diagdown\diagup}}^{H}\text{N"}$$
and substitute
$$-- \text{N}\underset{\underset{SCH_3}{|}}{\underset{C}{\diagdown\diagup}}^{H}\text{N} --$$

Signed and Sealed this

Twenty-sixth Day of May, 1992

Attest:

DOUGLAS B. COMER

*Attesting Officer*  *Acting Commissioner of Patents and Trademarks*